United States Patent [19]

Snorrason

[11] Patent Number: 5,312,817

[45] Date of Patent: May 17, 1994

[54] TREATMENT OF FATIGUE SYNDROME

[76] Inventor: Ernir Snorrason, Stigahlid 80, 105 Reykjavík, Iceland

[21] Appl. No.: 883,038

[22] Filed: May 14, 1992

[30] Foreign Application Priority Data

May 14, 1991 [IS] Iceland .................................. 3706/91
Feb. 13, 1992 [DK] Denmark ............................... 181/92

[51] Int. Cl.⁵ ..................... A61K 31/66; A61K 31/55; A61K 31/44; A61K 31/40
[52] U.S. Cl. ................................... 514/141; 514/142; 514/215; 514/217; 514/297; 514/346; 514/411; 514/923
[58] Field of Search ............... 514/141, 215, 297, 346, 514/411, 142, 217

[56] References Cited

FOREIGN PATENT DOCUMENTS 0098975 1/1984 European Pat. Off. .
0236684 9/1987 European Pat. Off. .
WO88/08708 11/1988 European Pat. Off. .

OTHER PUBLICATIONS

Chemical Abstracts, vol. 47, No. 6959 (1952).
"A Report-Chronic Fatigue Syndrome: Guidelines for Research," Journal of the Royal Society of Medicine, vol. 84, Feb. 1991; pp. 118-121.
Paskov, "Galanthamine", Handbook Exp. Pharmac., 79, pp. 653-672, 1986.
Bretagne and Valetta, "Essais Clinques en Anesthesiologie D'un Nouvel Anticholinesterasique La Galanthamine" (in French), Anesth. Analges, 22, pp. 285-292, 1965.
L. Wislicki, "Nivalin (Galanthamine Hydrobromide), An Additional Decurarizing Agent, Some Introductory Observations," Brit. J. Anaesth., 39, pp. 963-968, 1967.
D. A. Cozanitis and E. Toivaeea, "A Comparative Study of Galanthamine Hydrobromide and Atropine/-Neostigmine in Conscious Volunteers," Der Anaesthesist, pp. 416-421, 1971.
T. Thomsen and H. Kewitz, "Selective Inhibition of Human Acetylcholinesterase by Galanthamine In Vitro and In Vivo," Life Sciences, vol. 46, pp. 1553-1558, 1990.
T. Thomsen, U. Bickel, J. P. Fischer, H. Kewitz; "Galanthamine Hydrobromide in a Long-Term Treatment of Alzheimer's Disease," Dimentia, 1:46-51, pp. 46-51, 1990.
T. Thomsen, H. Kewitz, O. Pleul; "Estimation of Cholinesterase Activity (EC 3.1.1.7; 3.1.1.8) in Undiluted Plasma and Erythrocytes as a Tool for Measuring In Vivo Effects of Reversible Inhibitors," J. Clin. Chem. Clin. Biochem., 26, pp. 469-475, 1988.
S. Straus, "History of Chronic Fatigue Syndrome," Reviews of Infectious Diseases, vol. 13, Supplement 1, pp. S2-S7, Jan.-Feb. 1991.
D. Buchwald and A. Komaroff, "Review of Laboratory Findings for Patients with Chronic Fatigue Syndrome," Reviews of Infections Diseases, vol. 13, Supplement 1, S12-S18, Jan.-Feb. 1991.
N. M. Gantz and G. P. Holmes, "Treatment of Patients with Chronic Fatigue Syndrome," Drugs, vol. 38, No. 6, pp. 855-862, 1989.
M. Jindal, "Effect of Methylated Xanthines on Skeletal Muscle", B.J. Medical College, Jan., 1976. D. A. Bruckenstein, The Nerve Terminal Sinauer Associates, Inc., pp. 172-175.
Chemical Abstracts 81:9686h (1974).

Primary Examiner—Frederick E. Waddell
Assistant Examiner—T. J. Criares
Attorney, Agent, or Firm—Foley & Lardner

[57] ABSTRACT

The use of a pharmaceutically acceptable cholinesterase inhibitor or a prodrug therefor for the treatment of fatigue syndromes, including chronic fatigue syndrome, post-infectious fatigue syndromes, fatigue syndromes associated with human immunodeficiency virus (HIV) infection or with preeclampsia. The acetyl cholinesterase is preferably one that acts substantially selectively at nicotinic receptor sites, and which has selectivity for acetyl cholinesterase as opposed to butyryl cholinesterase. Compounds of the invention include galanthamine and galanthamine derivatives.

36 Claims, 2 Drawing Sheets

TREATMENT OF FATIGUE SYNDROME

SUMMARY OF THE INVENTION

The present invention relates to the use of pharmaceutically acceptable acetylcholinesterase inhibitors for the preparation of a pharmaceutical composition for treatment of fatigue syndromes, particularly a fatigue syndrome, such as Chronic Fatigue Syndrome (CFS), Post-infectious Fatigue Syndrome, fatigue associated with human immunodeficiency virus infection and related syndromes such as fatigue associated with preeclampsia. Preferably, the cholinesterase inhibitors are selected from a group of nicotinic acetylcholinesterase inhibitors such as galanthamine-hydrobromide, which are able to cross the blood brain barrier in humans.

DETAILED DESCRIPTION OF INVENTION

Fatigue Syndrome

Fatigue syndrome designates a condition where fatigue (or synonyme thereof including tiredness and weariness) is considered to be the principal symptom of uncertain cause, i.e. that no recognized underlying disease causes the fatigue. Fatigue is commonly reported as having two aspects, namely mental fatigue and physical fatigue, where mental fatigue is a subjective sensation characterized by lack of motivation and of alertness and physical fatigue is the feeling as lack of energy of strength and is often felt in the muscles.

To be regarded as a symptom, fatigue must be complained of, and should affect the person's functioning and be disproportionate to exertion. Furthermore, it should represent a clear change from a previous state and be persistent, or, if intermittent, should be present more than 50% of the time.

Fatigue should be distinguished from low mood and from lack of interest. The symptom of fatigue should not be confused with impairment of performance as measured by physiological or psychological testing. The physiological definition of fatigue is a failure to sustain muscle force or power output.

Fatigue syndromes have only recently been considered as "real" independent diseases and not only as being caused by an underlying disease or being complaints from neurotics or hypochondriacs. There is an increasing interest for finding the cause of the fatigue in order to find a medical treatment. However, an effective medical treatment for fatigue syndromes has not been available until now.

The study of fatigue performed by the present inventor indicates that the mechanism of fatigue could be an imbalance in the cholinergic nicotinic transmitter system, both peripherally and centrally, actually a decrease of acetylcholine in the central and peripheral synapses. This is supported by the facts that several of the symptoms often related to a fatigue syndrome are also thought to be caused by decrease of acetylcholine, the other symptoms being, e.g. disturbances of sleep.

The fatigue and the other symptoms of the syndromes are contemplated to result from an augmentation of the acetylcholinesterase in the synapsis which decreases the amount of synaptic acetylcholine, which decrease is a physiological response to infections and inflammations (sterile infections) because inflammations and infections cause a decrease in the $Ca^{2+}$ concentration and as explained below, the result in a decrease in the amounts of acetylcholine released from the presynaptic membranes.

EP 098 975 discloses a biostimulant tonic which comprises, as the active biostimulants, creatine and hydrolyzate of protein. The biostimulant contains 40 to 45% by weight of creatine, 42 to 46% by weight of calciummagnesium salt of inositephosphoric acid, 10 to 12% by weight of lyophilized hydrolysate of Royal Jelly, and 1 to 3% of galanthamine. The present invention does not encompass such tonic. EP 098 975 does not describe any phenomenon which corresponds to fatigue syndrome.

Cholinergic System

Many cell membranes can be excited by specific chemical or physiological stimuli. The common features of these processes and others carried out by excitable assemblies are:

1) The stimulus is detected by a highly specific protein receptor, which is an integral component of the excitable membrane.

2) The specific stimulus elicits a conformational change in the receptor. As a result, the permeability of the membrane or the activity of a membrane-bound enzyme changes. Many of the responses are highly amplified.

3) The conformational changes in the receptor and the resulting alterations in function are reversible. There are mechanisms that take the receptor back to its resting state and restore its excitability.

Nerve cells interact with other nerve cells at junctions called synapses. Nerve impulses are communicated across most synapses by chemical transmitters, which are small, diffusable molecules such as acetylcholine and norepinephrine. Acetylcholine is also the transmitter at motor end plates (neuromuscular junctions), which are the junctions between nerve and striated muscle.

The presynaptic membrane of a cholinergic synapse, that is one that uses acetylcholine as the neurotransmitter, is separated from the postsynaptic membrane by a gap of about 500 Å, called the synaptic cleft. The end of the presynaptic axon is filled with synaptic vesicles containing acetylcholine. The arrival of a nerve impulse leads to the release of acetylcholine into the cleft. The acetylcholine molecules then diffuse to the postsynaptic membrane, where they combine with specific receptor molecules. This produces a depolarization of the postsynaptic membrane, which is propagated along the electrically excitable membrane of the second nerve cell. Acetylcholine is hydrolyzed by acetylcholinesterase and the polarization of the postsynaptic membrane is restored.

Acetylcholine is synthesized near the presynaptic end of axons by the transfer of an acetyl group from acetyl CoA (Co-enzyme A) to choline. Some of the acetylcholine is taken up by synaptic vesicles, whereas the remainder stays in the cytosol. A cholinergic synaptic vesicle, which is typically 400 Å in diameter, contains about $10^4$ acetylcholine molecules.

Acetylcholine is released from the presynaptic membrane in form of packets containing of the order of $10^4$ molecules. The number of packets release depends on the potential of the presynaptic membrane. In other words the release of acetylcholine is an electrically controlled form of secretion.

Release of acetylcholine depends on the presence of $Ca^{2+}$ in the extracellular fluid. The depolarization of the presynaptic membrane leads to the entry of $Ca^{2+}$, which promotes a transient fusion of the synaptic vesicle membrane and the presynaptic membrane.

If the concentration of $Ca^{2+}$ is decreased, the presynaptic action potential releases fewer packets of acetylcholine; the number released depends on the $Ca^{2+}$ concentration. The size of the packets released are the same, it is the amount of packets that are depending on the $Ca^{2+}$ concentration. Thus, the amplitude of the potential of the postsynaptic membrane is depending on the $Ca^{2+}$ concentration in the surroundings of the presynaptic membrane.

The depolarizing signal may be switched off to restore the excitability of the postsynaptic membrane. Acetylcholine is hydrolyzed to acetate and choline by acetylcholinesterase. Acetylcholinesterase is located in the synaptic cleft, where it is bound to a network of collagen and glycosaminglycans derived from the postsynaptic cell. The 260-kdal enzyme, which has an $\alpha_2\beta_2$ structure, can be readily separated from the acetylcholine receptor.

Acetylcholinesterase has a very high turnover number of $25,000s^{-1}$, which means that it cleaves an acetylcholine molecule in 40 $\mu$sec. The high turnover number of the enzyme is essential for the rapid restoration of the polarized state of the postsynaptic membrane. Synapses can transmit 1,000 impulses per second only if the postsynaptic membrane recovers its polarization within a fraction of a millisecond.

Acetylcholine reacts with a specific serine residue at the active side of acetylcholinesterase to form a covalent acetyl-enzyme intermediate, and choline is released. The acetyl-enzyme intermediate then reacts with water to form acetate and regenerate the free enzyme.

Postsynaptic acetylcholine receptors may be assigned to two classes which are clearly pharmacologically distinguishable. Receptors that can be stimulated by nicotine are of the nicotinic type and may be blocked by curare, and receptors that can be stimulated by muscarine are of the muscarinic type and are insensitive to curare. In the autonomic nervous system, the nicotinic receptors are found in the ganglia whereas the muscarinic receptors are found in the effector organs.

Acetylcholinesterase is found at postsynaptic membranes, but also in the erythrocytes and in the plasma (so-called un-specific acetylcholinesterase or pseudocholinesterase or butyrylcholinesterase).

Acetylcholinesterase inhibitors enhance the effect of acetylcholine by inhibiting its hydrolyzation or at least prolonging the actual time that each acetylcholine molecule is present in the synapse. Cholinesterase inhibitors are of course understood as synonymous to anticholinesterase, and may be understood as a cholinesterase agonist.

Cholinergic synapses are found in the motor and plates (neuromuscular junctions), in the sympathetic part of the autonomic nervous system in all ganglionic synapses, at the synapses in the adrenal medulla, and at the postsynaptic synapses in the sweat glands. In the parasympathetic autonomic nervous system acetylcholine is the transmitter in all the ganglia as well as at postganglionic effector synapses. Furthermore, acetylcholine is present in the central nervous system where it is contemplated to function as a transmitter.

The therapeutic need for compounds capable of treating the fatigue syndrome has been increased with the understanding of the fatigue syndromes.

It has now been found that on administration of galanthamine, a cholinesterase inhibitor, the fatigue disappears, the time for disappearance of the fatigue generally being proportionate to the time the fatigue has lasted.

The present invention is based on the above-mentioned discovery and relates to the use of a cholinesterase inhibitor for the preparation of a pharmaceutical composition for the treatment of fatigue syndromes, such as severe fatigue syndromes, in particular Chronic Fatigue Syndrome, Post-infectious Fatigue Syndrome, fatigue associated with human immunodeficiency virus (HIV) infection, or fatigue related to preeclampsia. The cholinesterase inhibitor is preferably one which crosses the blood-brain barrier and furthermore is selective with respect to cholinergic nicotinic receptor sites, such as galanthamine hydrobromide.

A cholinesterase inhibitor is understood as being a synonym to an anticholinesterase, and furthermore, to be understood as an cholinergic agonist or a cholinergicum.

In the present context, the term "a syndrome" designates a complex of symptoms which appear so regularly together that it is contemplated that they are different signs of the same disease. The symptoms need not all appear always in all persons suffering from the syndrome, such as will appear from the following.

A fatigue syndrome is a syndrome where fatigue is always present as a principal symptom often accompanied by other symptoms as described below.

One example of a fatigue syndrome is the Chronic Fatigue Syndrome. The term "Chronic Fatigue Syndrome" has recently been agreed upon (Journal of the Royal Society of Medicine, Volume 84, February 1991) as a standard term with a distinct meaning, but the disease has been known for many years under other names such as, epidemic neuromyasthesia, idiopathic chronic fatigue and myalgia syndrome, chronic infectious monucleosis, benign myalgic encaphalomyelitis, post-viral fatigue syndrome, fibrositis-fibromyalgia syndrome, Icelandic disease, Akurayri disease, or Royal Free Hospital disease.

According to the above-mentioned agreement, The Chronic Fatigue Syndrome is defined by the following symptom:

A fatigue which is the principal symptom, which has a definite onset, and is severe, disabling and affects both physical and mental functioning, and furthermore the fatigue should have been present for a minimum of 6 months at which it was present for more than 50% of the time and by one or more of the following symptoms which may or may not be present:

Sleep disturbances, which are changes in the duration of sleep and/or quality of sleep. The changes could be hypersomnia or increased sleep, or insomnia or reduced sleep, (which should further be described as either difficulty of getting off to sleep, early wakening, or subjectively disturbed or unrefreshening sleep). The changes of the quality of sleep is contemplated to be due to a decrease in REM sleep, e.g. the deep sleep which is necessary for a feeling of having a good and refreshening sleep.

Disability, which refers to any restriction or lack (resulting from loss of psychological or physiological function) of ability to perform an activity in the manner or within the range considered normal for human being, i.e. things that people cannot do in the areas of occupational, social and leisure activities because of their illness. The disability should be distinguished from impairment of function (e.g. weak legs) and from handicap (e.g. unable to work). Furthermore, there should be a definite and persistent change from a previous level of functioning.

Mood disturbances such as depressed mood, anhedonia, anxious mood, emotional lability and irritability, the severity of the mood disturbances should be assessed on standard scales. Furthermore it should be determined whether the disorder is sufficient to meet the diagnostic criteria for major depressive disorders.

Myalgia, which is pain or aching felt in the muscles. The myalgia should be disproportionate to exertion. It should be distinguished from feelings of weakness and pain felt in other areas such as the joints.

In the present context, the term "fatigue syndrome" designates a syndrome which, qualitatively, that is, with respect to the character of the syndrome, is substantially identical to the condition characterized in the Chronic Fatigue Syndrome, but which quantitatively, that is, with respect to the duration of the syndrome, has not yet, at the time of treatment, lasted for the 6 months which constitute a compulsory element of the definition of the Chronic Fatigue Syndrome.

Thus, if a patient shows symptoms which, had they prevailed for at least 6 months, would categorize the patient as suffering from the Chronic Fatigue Syndrome, but which have not yet, at the time in question, prevailed for 6 months, the shorter duration, although bringing the syndrome outside the established definition of Chronic Fatigue Syndrome, does not bring the condition outside the definition of fatigue syndrome as used herein.

With reference to the definition of the Chronic Fatigue Syndrome, the fatigue syndrome definition used herein will, thus, at least comprise the same disabling fatigue condition which (if it has lasted for at least 6 months) already in itself would establish a condition under the definition of the Chronic Fatigue Syndrome.

Normally, however, a fatigue condition will not be considered a syndrome unless it has had a duration and/or a course which distinguishes it from, e.g., the fatigue resulting from normal exertion. Thus, fatigue syndrome in the sense of the present specification is one which is complained of, significantly affects the person's functioning, and represents a clear change from a previous state. Its duration will have been at least 14 days, normally at least one month. In the present specification and claims, a severe fatigue syndrome is defined as a fatigue syndrome the duration of which is at least 2 months, normally at least 3 months.

Another example of a fatigue syndrome is the Post-infectious Fatigue Syndrome which may be considered as a subclass of the Chronic Fatigue Syndrome. The Post-infectious Fatigue Syndrome is defined by the same symptoms as the Chronic Fatigue Syndrome and furthermore, a definite evidence of infection at onset must have been provided and the infection should have been corroborated by laboratory evidence.

Yet another example of a fatigue syndrome is the fatigue associated with human immunodeficiency virus (HIV) infection (AIDS).

A still further fatigue syndrome is the syndrome associated with preeclampsia.

As appears from the above, the crucial feature of the present invention is the administration of a cholinesterase. Compounds which function as cholinesterase inhibitors may be divided into several groups, namely poison gases for use in warfare, insecticides, such as malathion, and drugs. In the present context, the term "pharmaceutically acceptable" indicates that the cholinesterase inhibitors in question are not such which will be poisonous, in other words, they pertain to the drug group and not to the poison group.

Pharmaceutically acceptable cholinesterase inhibitors are, e.g., galanthamine and galanthamine derivatives, norgalanthamine and norgalanthamine derivatives, epigalanthamine and galanthamine, physostigmine, tacrine and tacrine analogues, fasciculin, metrifonate, heptyl-physostigmine, norpyridostigmine, norneostigmine, and huperzine or a prodrug therefor. Some of the cholinesterase inhibitors show certain undesirable properties, such as short half life, etc. In some cases, such deficiencies can be compensated for by modifying the compound into a prodrug for the active compound, in accordance with well-known principles for prodrug construction, such as introduction of hydrophilic groups to enhance the solubility of a compound in water, thus making it possible to formulate the compound as a an injection solution, an introduction of lipophilic groups such as ester groups to enhance the capability of the compound to pass the blood-brain barrier. The presently preferred cholinesterase inhibitor used according to the invention is galanthamine. Galanthamine is known as an acetylcholinesterase acting substantially only at nicotinic receptor sites, that is, having a high selectivity for acetylcholinesterase as opposed to butyrylcholinesterase. A more detailed discussion of galanthamine and galanthamine derivatives is given below:

Galanthamine is a well-known acetylcholinesterase inhibitor which is active substantially selectively at nicotinic receptor sites and has substantially no effect on muscarinic receptor sides, is capable of passing the blood-brain barrier in humans, and presents no severe side effects in therapeutically necessary dosages.

Galanthamine and acid addition salts thereof have, for many years, been known to have anticholinesterase properties.

Galanthamine, a tertiary alkaloid, has been isolated form the bulbs of the Caucasian snowdrops Galantanus woronowi (Proskurnina, N. F. and Yakoleva, A. P. 1952, Alkaloids of Galanthus woronowi. II. Isolation of a new alkaloid. (In Russian.) Zh. Obschchei Khim. (J.Gen.Chem.) 22, 1899–1902.

Chem.abs. 47,6959, 1953. It has also been isolated from the common snowdrop Galanthus Nivalis (Boit, 1954).

Galanthamine has been used extensively as a curare reversal agent in anaesthetic practice in Eastern bloc countries (cf. review by Paskow, 1986) and also experimentally in the West (cf. Bretagne and Valetta, 1965: Wislicki, 1967; Consanitis, 1971).

Pharmacokinetic studies have recently been made by Thomsen, T. and H. Kewitz. (Selective Inhibition of Human Acetylcholinesterase by Galanthamine in vitro and in vivo. Life Sciences, Vol 46, pp. 1553–1558 (1990), and, by the same authors, Galanthamine Hydrobromide in a Long-Term Treatment of Alzheimer's Disease. Dementia 1990, 1:46–51).

It is believed that the excellent and surprising affect possessed by galanthamine is due to its specific profile of properties, the most important of the known ones of which can be summarized as follows:

capability to pass the blood brain barrier in humans, a high selectivity for acetylcholinesterase as opposed to butyrylcholinesterase (about 50-fold when measured by the in vitro method by Thomsen et al., see below), a sufficient elimination half life to warrant duration of an effective concentration of at least 4 hours, probably at least 6 hours, a relatively low toxicity in therapeutical concentrations, capability of being effective in doses which are sufficiently low to keep peripheral side effects low.

Galanthamine must be considered as being a very desirable drug for the treatment according to the invention: The elimination half life of galanthamine hydrobromide is over four hours; it shows a practically complete renal elimination. A complete elimination of metabolites and galanthamine takes place in 72 hours. Galanthamine has been used in Eastern Block countries since around 1958 as an anticurare agent in anesthesiology, and a considerably number of patients have been treated with galanthamine without any reported case of liver toxicity or serious side effects. Galanthamine hydrobromide, being a tertiary amine and lipid soluble, is absorbed rapidly from the gut and transverses the blood brain barrier easily. The common side effects, other than the ones related to cholinergic crisis, are either nausea or vomiting, and a slight headache. However, these side effects are rare, especially when care is taken to start medication in low doses such as mentioned above.

The galanthamine can suitably be administered orally in the form of an acid addition salt, e.g. the hydrobromide, but other administration forms are possible and realistic, such as is described below.

Because galanthamine has substantially no effect on the activity at muscarinic receptor sites, as apparent from its high selectivity for acetylcholinesterase as opposed to butyrylcholinesterase, it will not give rise to the often severe side effects on the heart which are associated with cholinesterase inhibitors which have a low selectivity for acetylcholinesterase as opposed to butyrylcholinesterase. Galanthamine has an in vitro selectivity for acetylcholinesterase opposed the effect on butyrylcholinesterase of 50 to 1, as reported by Thomsen, Life Sciences, Vol 46, pp. 1553-1558 (1990).

As indicated above, the amount of galanthamine is preferably adjusted individually based upon observation of the effect of initially very low dosages. There is as considerable able difference with respect to how sensitive individuals are to acetylcholinesterase inhibitors. Thus, the amount of galanthamine is suitably adjusted by means of a regimen starting at low dosages, e.g. 1 mg, preferably at 5 mg, per day, but, if appropriate. even as low as 0.1 mg per day, if the dosage is well tolerated by the patient within the first two hours the dosages is increased to, e.g. 10 mg per dosage dosed 3 to 4 times per day or in some severe cases to 60 mg or more per day dosed over 3 or 4 times.

Because cholinergic crisis, a life-threatening dose-dependant side effect of all kinds of acetylcholinesterase inhibitors, should, by all means, be avoided, it is recommended to start with the low dosages as mentioned above and furthermore not to exceed 150 mg per day and preferably not to exceed dosages above 60 mg per day, unless the patient shows a very low sensitivity to acetylcholinesterase inhibitor, in which case higher doses, such as 200 mg per day, could be used.

The treatment according to the invention should preferably be continued at least for two months, such as, e.g., three months, or until the syndrome has disappeared.

While galanthamine has, indeed, given remarkable results, such as appears from the clinical cases given in the examples, it is justified to presume that other acetylcholinesterase inhibitors which are functional equivalents to galanthamine with respect to its combination of high selectivity with respect to nicotinic receptor sites and capability of passing the blood brain barrier in humans in vivo, will also show a useful combination of effect against fatigue syndrome and acceptability in the clinic, although it cannot be ruled out that galanthamine, galanthamine salts and galanthamine derivatives, due to the special conformation of the galanthamine ring system, have specific properties which are decisive for the remarkable effect.

In accordance with the above, compounds which are functional equivalents of galanthamine are defined herein as compounds which a) possess an at least 10-fold selectivity, preferably an at least 20-fold selectivity, more preferably an at least 40-fold selectivity, and most preferably an at least 50 fold selectivity, for acetylcholinesterase as opposed to butyrylcholinesterase, when measured by the in vitro method by Thomsen et al., see below, b) are capable of passing the blood brain barrier in humans in vivo.

As will be understood from the above definition, a compound can be subjected to well-defined and relatively shortlasting tests (see below) to determine whether it fulfills criterion a) above. Then, the likelihood whether the compound will pass the blood brain barrier in humans in vivo (criterion b)) can be assessed in a model. One such model is a whole rat brain model in which rats are given the acetylcholine esterase in vivo and are then killed whereupon homogenate of the rat brain is examined with respect to the acetylcholinesterase activity; the result is then compared to the acetylcholinesterase activity in rat brains not treated with acetylcholinesterase inhibitors. Another rat model could be the measurement and comparison of acetylcholinesterase activity in cerebrospinal fluid in vivo in the same rat before and after treatment. If the compound fulfills criterion a), and its likelihood of passing the blood brain barrier has been established in one of the above-described rat brain models, it will be a candidate drug. An initial determination of toxicity is necessary in cases before any effect in humans can be assessed; such initial determination of toxicity can be performed by pharmacologic tests in a manner known per se. After the pharmacological tests, the capability of the candidate drug of passing the blood brain barrier in humans in vivo can be determined by the method described below. If the candidate drug has been found to possess this capability, it can be passed to the testing proper. Optionally, the candidate drug can be subjected to additional short-lasting tests, such as the in vivo selectivity test described by Thomsen et al., and a test to determine whether it increases cortisol level in humans. Both of these tests give further indication of whether the candidate drug has a spectrum of properties equivalent to galanthamine with respect to what must be presumed to be essential properties. Peripheral side effects will be assessable when the effect is tested clinically, which is acceptable from an experimental and ethical point of view, provided the toxicity has first been assessed by the above-mentioned pharmacological tests. With respect to the final assessment of the candidate drug's effect on fatigue syndrome, a rational and efficient design of the assessment will involve an initial test on one or a few patients and, provided the initial test is positive, the above-mentioned conclusive double blind test. Because of the well-defined and brief character of all of the tests, and especially the well-defined in vitro character of the initial screening, the test series for identifying useful functional equivalents of galanthamine is a reasonable an not burdensome routine which is within the realm of the person skilled in the art.

Functional equivalents and derivatives of galanthamine which are useful in the method of the invention will be employed in the same manner as stated herein for galanthamine. Whenever quantities of such a functional equivalent or derivative are referred to herein, the quantities are given as the equipotent quantity of galanthamine hydrobromide with respect to inhibition of acetylcholinesterase, that is, as the quantity of galanthamine hydrobromide which results in the same inhibition of acetylcholine esterase in the above-mentioned in vitro test according to Thomsen et al as does the functional derivative or derivative.

The selectivity of the acetylcholinesterase inhibitor for acetylcholinesterase as opposed to butyrylcholinesterase can be determined by in vitro and in vivo tests as described by Thomsen and Kewitz in the above mentioned paper Selective Inhibition of Human Acetylcholinesterase by Galanthamine in vitro and in vivo, Life Sciences, Vol 46, pp. 1553–1558 (1990), and T. Thomsen, H. Kewitz and O. Pleul, J. Clin. Chem. Clin. Biochem. 26 469–475 (1988). The in vitro test described by Thomsen and Kewitz in Life Sciences, Vol 46, pp 1553–1558 (1990) is the one referred to above in connection with criterion a) and whenever numeric (10-fold, 20-fold, 40-fold) reference to selectivity for acetylcholinesterase as opposed to butyrylcholinesterase is made in the claims. According to Thomsen and Kewitz, galanthamine hydrobromide, when tested under the conditions described, shows a 50-fold selectivity; this selectivity value is taken as the "fixpoint" whenever in vitro selectivities are discussed herein and could be used, for the purpose of determining the selectivities for other cholinesterase inhibitors, as a calibration value which is the one to establish with galanthamine hydrobromide in any repetition of the experiment described by Thomsen and Kewitz. Thus, with reference to this determination method, a preferred acetylcholinesterase inhibitor is one which in the in vitro method described has an at least 10-fold selectivity for acetylcholinesterase as opposed to butyrylcholinesterase, such as an at least 20-fold selectivity for acetylcholinesterase as opposed to butyrylcholinesterase, e.g. an at least 40-fold selectivity for acetylcholinesterase as opposed to butyrylcholinesterase.

A relatively easy commercially available selectivity test which can be used as a practical tool in the screening of candidate drugs is the test described in Example 1 herein.

The capability to pass the blood brain barrier in vivo in humans can be assessed by either by a test which could be called "Auditory brain stem response" or by a test which is based on the measurement of CRH, ACTH and cortisol. The rationale behind these tests, and the way they are performed, is explained in the following:

The auditory brain stem response test is based on the observation that manio-depressive patients are hypersensitive to cholinergic influences, one manifestation hereof being hypersensitivity to auditory signals as assessed by the increase of amplitude of auditory evoked potentials in the nuclei of the auditory system in the brain stem, i.e. on the "brain side" of the blood brain barrier. This hypersensitivity manifests itself in a lower amplitude than in normal humans when the person is not treated with a cholinergic agent such as acetylcholinesterase inhibitor; and a very significantly increase of the amplitude when the person has received a cholinergic agent, provided, of course, that the cholinergic agent is able to pass the blood brain barrier and thus enter the nuclei of the auditory system in the brain stem. See also example 3.

The other test based on the measurement of CRH (corticotropic-hormone releasing hormone released from the hypothalamus in the brain, and which releases both ACTH from the adenohypophysis and cortisol from the adrenal medulla) and ACTH (corticotropic hormone, which releases cortisol from the adrenal medulla) is carried out by measuring the CRH, ACTH and cortisol concentration in the blood in healthy persons before and after medication with acetylcholinesterase. If the concentration of all three hormone are increased after medication or at least CRH and cortisol are increased it is proven that the acetylcholinesterase has effect in the central nervous system, and since it is an in vivo experiment it is further proven that the acetylcholinesterase has passed the blood brain barrier.

As mentioned above, the selectivity of the acetylcholinesterase inhibitor can, as an additional characterization, optionally be expressed with reference to the in vivo determinations performed by Thomsen and Kewitz on galanthamine and described in the above-mentioned paper Selective Inhibition of Human Acetylcholinesterase by Galanthamine in vitro and in vivo, Life Sciences, Vol 46, pp. 1553–1558 (1990). With reference to this determination, a preferred acetylcholinesterase inhibitor is one which, upon administration in an amount of 10 mg to a healthy adult, results in inhibition of at least 40% of the acetylcholinesterase activity in erythrocytes from the adult within about 2–5 minutes and no substantial inhibition of butyrylcholinesterase therein, such as an acetylcholinesterase inhibitor which, when administered in an amount of 10 mg to a healthy adult, results in inhibition of at least 50% of the acetylcholinesterase activity in erythrocytes from the adult within about 2–5 minutes. For galanthamine, Thomsen and Kewitz found 65% inhibition of acetylcholinesterase in the erythrocytes within 2 minutes after administration of 10 mg of galanthamine i.v. in a healthy volunteer, whereas no inhibition of butyrylcholinesterase in plasma was seen. Also these determinations are referred to in claims herein and should, in connection with the evaluation of the corresponding selectivities of candidate drugs different from galanthamine hydrobromide be considered the "calibration fixpoints" which will be established with galanthamine hydrobromide in any repetition of this experiment.

As mentioned above, it is possible that galanthamine, galanthamine salts and galanthamine derivatives, due to the special conformation of the galanthamine ring system, have specific properties which are decisive for the remarkable effect established according to the present invention. Thus, according to one aspect of the invention, compounds which are contemplated to be valuable and useful in the treatment according to the invention are the compounds having the formula I (formula I also represent galanthamine itself)

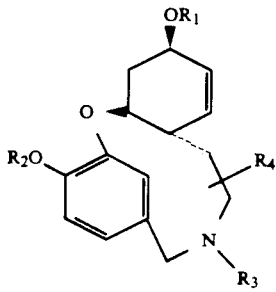

wherein $R^1$ and $R^2$ which may be the same or different each represents a hydrogen atom or an acyl group, such as a lower alkanoyl group, e.g. an acetyl group or a straightchained or branched alkyl group, e.g. methyl, ethyl, propyl, or isopropyl; $R^3$ is a straight or branched chain alkyl, alkenyl or alkaryl group which is optionally substituted by a halogen atom or a cycloalkyl, hydroxy, alkoxy, nitro, amino, aminoalkyl, acylamino, heteroaryl, heteroaryl-alkyl, aroyl, aroylalkyl or cyano group; and $R^4$ represents a hydrogen or halogen atom attached to at least one of the ring carbons of the tetracyclic skeleton, with the proviso that when $R^4$ is in a position neighbouring the nitrogen atom, then $R^4$ is preferably different from halogen, and salts thereof, such as a hydrobromide, hydrochloride, methylsulphate or methiodide.

In the compounds of formula I, alkyl moieties preferably contain 1 to 8 carbon atoms, halogen atoms are preferably fluorine, chlorine, or bromine, especially fluorine or chlorine, aryl moieties are preferably phenyl, cycloalkyl groups are preferably 3- to 7-membered rings, especially cyclopropyl or cyclobutyl, and heteroaryl moieties are preferably 5- to 8-membered rings, e.g., thienyl, furyl, pyridyl, pyrrolyl, or pyrizanyl.

Among the compounds of the formula I are those described in EP-A-236684. The compounds of formula I may be prepared according to conventional techniques, including those described in EP-A-236684.

A broader range of compounds which, from the point of view of structural similarity with galanthamine, are contemplated to be valuable compounds useful in the method of the invention are galanthamine derivatives of the general formula II

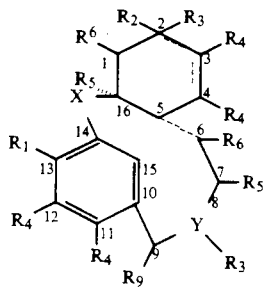

wherein the broken line represents an optionally present double bond in one or the two of the positions shown, $R_1$ and $R_2$ are each selected independently from the group consisting of hydrogen, hydroxyl, amino or alkylamino, cyano, sulfhydryl, alkoxy of 1-6 carbon atoms, alkylthio, aryloxy, arylthio, $R_5$-substituted aryloxy, $R_5$-substituted arylthio, aralkoxy, an aliphatic or aryl carbamyl group wherein the aliphatic or aryl moiety may be $R_5$ substituted or unsubstituted, aralkylthio, $R_5$-substituted aralkoxy, $R_5$-substituted aralkylthio, aryloxymethyl, $R_5$-substituted aryloxymethyl, alkanoyloxy, hydroxy-substituted alkanoyloxy, benzoyloxy, $R_5$-substituted benzoyloxy, aryloxycarbonyl and $R_5$-substituted aryloxycarbonyl, $R_1$ may also be alkyl of up to 14 carbon atoms, or hydroxymethyl, $R_2$ may also be carboxymethyl, provided that at least one of $R_1$ and $R_2$ is hydroxy, amino or alkylamino unless $R_8$ is hydroxymethyl, $R_3$ is hydrogen, straight or branched chain alkyl of 1-6 carbon atoms, cycloalkylmethyl, phenyl, $R_5$-substituted phenyl, alkylphenyl, $R_5$-substituted alkylphenyl, heterocyclyl selected from α- or β-furyl, α- or β-thienyl, thenyl, pyridyl, pyrazinyl, and pyrimidyl, alkyl-heterocyclyl or $R'$-substituted heterocyclyl, where $R'$ is alkyl or alkoxy, each $R_4$ is independently selected from hydrogen, hydroxyl, sulfhydryl, alkyl, aryl, aralkyl, alkoxy, mercaptoalkyl, aryloxy, thiaryloxy, alkaryloxy, mercaptoalkaryl, nitro, amino, N-alkylamino, N-arylamino, N-alkarylamino, fluoro, chloro, bromo, iodo, and trifluoromethyl, $R_5$ is selected from the same groups as $R_4$, $R_6$ is hydrogen, halo, trifluoromethyl or alkyl of 1 to 4 carbon atoms, with the proviso that when $R_6$ is in position 7 or 9, it is preferably not halo, $R_7$ is selected from the same groups as $R_4$ or may be hydroxyalkyl of 1-2 carbon atoms, $R_8$ is hydrogen or hydroxymethyl, $R_9$ is hydrogen or alkyl of 1 to 6 carbon atoms, or when $R_2$ is hydroxyl, $R_9$ may be a moiety of formula I wherein $R_9$ is hydrogen and $R_2$ is a linking bond; or $R_2$ and $R_9$ may jointly form semicarbazone, X is oxygen or $NR_5$, Y is nitrogen or phosphorus, and methylenedioxy derivatives thereof with the proviso that when X is O, $R_3$ is not methyl when $R_1$ is methoxy, $R_2$ is hydroxy, and all $R_4$ are hydrogen, or a pharmaceutically acceptable acid addition salt thereof.

Examples of subclasses and specific compounds of the formula II are given in WO 88/08708, which also discloses methods for preparing the compounds II.

Galanthamine, galanthamine salts, galanthamine derivatives and galanthamine functional equivalents, when suited therefor, may be administered orally at a dosage of e.g. 5-150 mg per day, such as 10-60 mg per day, e.g. 10-50 mg, such as 10-40 mg, per day, the dosage being adapted to the patient and the patient's response. As mentioned above, the treatment should often be started with a low dosage and then increased until the suitable dosage has been established. The dosage of galanthamine functional equivalents or galanthamine derivatives is expressed as the equipotent amount of galanthamine hydrobromide, the reference basis being the capability of inhibiting acetylcholinesterase in the Thomsen et al. in vitro test mentioned above.

Examples of parenteral administration ranges are 0.1–1000 mg per day, such as 5–1000 mg per day, e.g. 10–500 mg per day, including 50–300 mg per day; lower dosages are often preferred, such as 10–50 mg per day, e.g. 10–30 mg per day.

For the oral administration, galanthamine or a galanthamine salt or derivative or a functional equivalent may be formulated, for example, as an aqueous suspension or a solution in aqueous ethanol or as a solid composition such as a tablet or capsule. Suspensions or solutions for oral administration are typically of a concentration of 1–50 mg/ml, more commonly 5–40 mg/ml, for example, 10–40 mg/ml, typically 20–30 mg/ml of galanthamine. Divided doses into the range 0.5–5 mg/kg body weight per day are useful, in some situations divided doses in the range of 0,1–3 mg/kg body weight per day may also prove useful. Examples of dosages are up to 2000 mg per day, such as 0.1–2000 mg per day, or 5–2000 mg per day. Other ranges that should be mentioned are 100–600 mg per day or 10–500 mg per day, such as 10–50 or 10–30 mg per day. Typically, one might administer a dosage of 20–100 mg per day to a patient of a body weight of 40–100 kg, although in appropriate cases such dosages may prove useful for patients having a body weight outside this range. However, in other instances dosages of 50–300 mg per day to a patient of a body weight of 40–100 kg may be also be very useful. In other cases, dosages as low as 10 mg and as high as 200 mg may be appropriate for persons in this body weight range.

Galanthamine and its acid addition salts form crystals. They are generally only sparingly soluble in water at room temperature; therefore, injectable compositions are normally in the form of an aqueous suspension. If necessary, pharmaceutically-acceptable suspension aids may be employed. Typically, such a suspension will be employed at a concentration of 0.1–50 mg/ml, such as 1–50 mg/ml, more commonly 5–40 mg/ml, for example, 5–30 mg/ml or 10–40 mg/ml, such as 10–30 mg/ml, especially 20–30 mg/ml of galanthamine. As mentioned above, typical dosage rates when administering galanthamine by injection are the range 0.01–20 mg per day depending upon the patient. For example, divided doses in the range 0,5–5 mg/kg body weight per day may prove useful. Typically, one might administer a dosage of 5–50 mg per day to a patient of a body weight of 40–100 kg, although in appropriate cases such dosages may prove useful for patients having a body weight outside this range. In other cases, dosages as low as 5 mg and as high as 200 mg per day may be appropriate for persons in this body weight range.

Galanthamine and its pharmaceutically acceptable acid addition salts, and its derivatives and functional equivalents, when suited therefor, may be administered by subcutaneous, intravenous or intramuscular injection.

The parenteral dosage rate of galanthamine can also be expressed by reference to the body weight of the patient; in this case, a normal dosage rate will often be 0.1 to 4 mg/kg body weight. Depot compositions will often deliver a dosage rate of 0.01 to 5.0 mg/kg per day.

In preparing tablets or capsules, standard tablet or capsule-making techniques may be employed. If desired, a pharmaceutically acceptable carrier such as starch or lactose may be used in preparing galanthamine or galanthamine equivalent tablets. Capsules may be prepared using soft gelatine as the encapsulating agent. If desired, such capsules may be in the form of sustained release capsules wherein the main capsule contains microcapsules of galanthamine or functional equivalents thereof which release the contents over a period of several hours thereby maintaining a constant level of galanthamine or its functional equivalent in the patient's blood.

The following specific formulations may find use according to the invention:

Tablets or capsules containing 0.1, 1, 2, 5, 10 and 25 mg galanthamine hydrobromide or functional equivalent to be taken four times a day, or a sustained-release preparation delivering an equivalent daily dose.

Liquid formulation for oral administration available in 5 mg/ml and 25 mg/ml concentration.

Other interesting administration forms of galanthamine and functional equivalents are suppositories, a slow-release plaster, and other depot compositions.

All of the above-mentioned administration forms are prepared in manners known per se.

Although galanthamine must be considered as having a high degree of safety, there have been certain side effects in a few of the patients treated. These have been slight nausea in about 30% of the cases (the nausea, however, disappearing after about one week of treatment), vomiting and dizziness in 5–10% of the patients (also disappearing after about one week of treatment in most cases), and more severe side effects in 4–6% of the patients. These more severe side effects must be considered acceptable in view of the effect of the drug; however, in patients who are suspected of developing arrhythmia, it should be considered to administer, e.g., atropine in combination with the treatment according to the invention.

The administration forms for the cholinesterase inhibitors, galanthamine, the galanthamine salts and the galanthamine derivatives may be orally and parenterally. The administration being dependent on the patient's age and weight, and on the daily life of the patient as well as the severity of the disease.

Parenteral administration may comprise suitable injection, e.g. intravenous, intramuscular, subcutaneous, as well as transdermal or rectally administration or implantation of e.g. suitable delivery devices, such as a intrathetical device.

Formulations for parenteral use may be a solution or suspension, a plaster for transdermal application, or a suppository.

EXAMPLE 1

Test for cholinesterase activity in blood samples

Method

SIGMA DIAGNOSTICS ® CHOLINESTERASE (PTC) kit, available from Sigma Diagnostics, can be used for determining the activity and selectivity of cholinesterase inhibitors. In the following, it is illustrated how the kit is used for the determination of the activity and selectivity of Nivalin (Galanthamine hydrobromide).

Reactions involved in the cholinesterase assay are as follows:

Propionylthiocholine + $H_2O$ 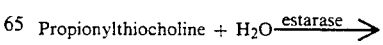

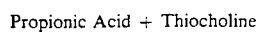

Thiocholine + 5,5'-Dithiobis-2-Nitrobenzoic Acid → 5-Thio-2-Nitrobenzoic Acid

5-Thio-2-Nitrobenzoic Acid is assessed by measuring the absorbance at 405 nm. The rate of change in absorbance at 405 nm is directly proportional to cholinesterase activity.

The activity of erythrocyte cholinesterase may be calculated on the basis of the measurement of butyrylcholinesterase (pseudocholinesterase) in serum and cholinesterase in hemolyzed whole blood (hemolysate), both measured simultaneously by the method described above, and evaluated according to the hematocrit value according to the formula $$HChE = (EChE \times Hct^*) + (PChE \times (1 - Hct^*))$$

Therefore, $EChE = \dfrac{HChE - (PChE \times (1 - Hct^*))}{Hct^*}$

*Hematocrit value expressed as decimal equivalent (i.e., 44% = 0.44).

In the above formulae, EChE is erythrocyte cholinesterase activity, PChE is plasma cholinesterase activity, HChE is hemolysate cholinesterase activity, and Hct is hematocrit value of the sample.

Another way of assessing the cholinesterase activity is to measure the plasma cholinesterase and the cholinesterase in purified hemolyzed erythrocytes. By doing this, the values are obtained directly.

Blood samples from 3 patients were tested with the Sigma test. The tests were carried out with samples where no Nivalin was added and with samples where 1.25 μg/ml Nivalin and 2.5 μg/ml were added in vitro. The results are shown below in table 1.1.

TABLE 1.1

| Nivalin added μg/ml | Hemolysate ChE activity | Serum ChE activity |
|---|---|---|
| 0 | 1.00 | 1.00 |
| 1.25 | 0.96 | 0.98 |
| 2.50 | 0.86 | 0.97 |

The results show a significant reduction of the hemolysate cholinesterase activity with increased concentration of galanthamine hydrobromide, whereas the data for the serum activity do not show any statistically significant change as a response to the addition of the galanthamine hydrobromide, which is an indication of a high selectivity of the galanthamine hydrobromide with respect to acetylcholinesterase as opposed to butyrylcholinesterase. Selectivity for acetylcholinesterase in erythrocytes opposed to butyrylcholinesterase is contemplated to reflect the selectivity for acetylcholinesterase at nicotinic receptor sites opposed to the acetylcholinesterase at muscarinic receptor sites.

This test may be used as a screening for candidate cholinesterase inhibitors with respect to their selectivity.

EXAMPLE 2

Formulations of Tablets Containing Galanthamine

| Composition of 1 tablet containing 1 mg galanthamine | |
|---|---|
| Galanthamine hydrobromide | 0.001 g |
| Calcium phosphate | 0.032 g |
| Lactose | 0.005 g |
| Wheat Starch | 0.0056 g |
| Microcrystalline Cellulose | 0.015 g |
| Talc | 0.0007 g |
| Magnesium Stearate | 0.0007 g |
| Composition of 1 tablet containing 5 mg galanthamine | |
| Galanthamine hydrobromide | 0.005 g |
| Calcium phosphate | 0.024 g |
| Lactose | 0.004 g |
| Wheat Starch | 0.004 g |
| Microcrystalline Cellulose | 0.04 g |
| Talc | 0.002 g |
| Magnesium Stearate | 0.001 g |
| Composition of 1 tablet containing 10 mg galanthamine | |
| Galanthamine hydrobromide | 0.010 g |
| Lactose | 0.040 g |
| Wheat Starch | 0.0234 g |
| Microcrystalline Cellulose | 0.0374 g |
| Talc | 0.0036 g |
| Magnesium Stearate | 0.0012 g |
| Gelatin | 0.0044 g |

Preparation

All the tablets are prepared according to routine tabletting procedures.

EXAMPLE 3

Diagnostic Criteria for Patients With the Chronic Fatigue Syndrome (CFS)

To diagnose Chronic Fatigue Syndrome a guideline for research has been published (5).

A syndrome characterized by fatigue as the principal syndrome.

A syndrome of definite onset that is not life long.

The fatigue is severe, disabling and affects physical and mental functioning.

The symptom of fatigue should have been present for a minimum of 6 months during which it was present for more than 50% of the time.

Other symptoms may be present, particularly myalgia, mood and sleep disturbances.

Certain patients should be excluded from the definition. They include:

Patients with established medical conditions known to produce chronic fatigue (e.g. severe anemia). Such patients should be excluded irrespective of whether the medical condition is diagnosed at presentation or only subsequently. All patients should have a history and physical examination performed by a competent physician.

Patients with current diagnoses of schizophrenia, manic depressive illness, substance abuse, eating disorder, or proven organic brain disease. Other psychiatric disorders (including depressive illness, anxiety disorders, and hyperventilation syndrome) are not necessarily reasons for exclusion.

EXAMPLE 4

Diagnostic Criteria For Patients With the Post-infectious Fatigue Syndrome (PIFS)

The patients must fulfill the criteria for CFS as defined above and should also fulfill the following criteria:

A definite evidence of infection at onset or presentation

The syndrome is present for at least 6 months after onset of the infection.

The infection has been corroborated by laboratory evidence.

EXAMPLE 5

Double-blind Cross-over Trial of the Effect of Calanthamine on Chronic Fatigue Syndrome (CFS)

Persons 20 persons suffering from Chronic Fatigue Syndrome fulfilling the criteria described in example 4 or 5.

Method

Each patient received treatment for a minimum of 8 weeks. The first 2 weeks incorporated an escalating schedule to stabilise the patient on an appropriate dose. The trial was running for eight weeks.

11 of the persons were randomly allocated to galanthamine treatment, and the remaining 9 to placebo treatment. The protocol for the trial made provisions for the clinician to opt after two weeks of treatment for transfer to the alternative treatment. The switch to the alternative treatment was made if he regarded the patient as having failed to benefit from the 2 weeks therapy.

The data available for the evaluation covered groups of patient-completed visual analogue scales to assess sleep disturbance, fatigue, myalgia, work capacity/-satisfaction, and dizziness, together with time per response on a visual search task.

Results

The results of the analysis of data from the visual analogue scales during the first two weeks of treatment are shown in table 6.1.

In order to assess any underlying, overall performance difference between the galanthamine and placebo treated patients, the median (the statistic which differentiates the upper and lower 50% of scores) of the changes across all scales, was computed for the placebo treated patients.

Using this median as an index of average "placebo response", it was found that 68.18% of galanthamine treated patients changes on the analogue scales fall above the placebo median, a difference (from the top 50% of placebo treated patients) which is statistically significant (exact p=0.033). This demonstrates an underlying trend for CFS patients treated with galanthamine to generate more beneficial changes on these visual analogue scales, which cannot be explained as a 'placebo response'.

Turning from the patients' own evaluation of therapeutic benefit, to the clinicians' assessment of response during the first two weeks of treatment, it was found that at this point all 9 of the patients randomly allocated to the placebo were transferred to galanthamine, whilst only 1 of the 11 patients receiving galanthamine was transferred to placebo treatment. Such a difference (i.e. 9/9 vs 1/11) is highly significant (exact p=0.00006). It is worth noting that the one patient transferred from galanthamine to placebo, after 2 weeks on placebo was found to have failed to respond and was returned to galanthamine.

TABLE 6.1

MEANS (STANDARD ERRORS) OF VISUAL ANALOGUE SCALES

| Scale | Treatment (N) | Baseline | After 1 Week | After 2 Weeks |
|---|---|---|---|---|
| Sleep Disturbance | Galanthamine (11) | 20.78 (2.13) | 17.90 (2.25) | 18.42 (2.09) |
| | Placebo (9) | 22.96 (1.34) | 19.51 (2.44) | 18.22 (2.96) |
| Fatigue | Galanthamine (11) | 29.41 (1.64) | 29.76 (1.70) | 25.21 (2.32) |
| | Placebo (9) | 28.52 (1.97) | 27.67 (2.26) | 26.53 (1.77) |
| Myalgia | Galanthamine (11) | 17.58 (0.74) | 15.95 (0.73) | 13.58 (1.26) |
| | Placebo (9) | 17.26 (0.71) | 16.03 (1.02) | 14.69 (0.95) |
| Work Capacity/ Satisfaction | Galanthamine (11) | 9.43 (1.17) | 11.61 (1.28) | 9.64 (1.61) |
| | Placebo (9) | 11.29 (0.99) | 10.80 (1.36) | 9.43 (1.21) |
| Memory | Galanthamine (11) | 5.31 (0.93) | 5.89 (0.90) | 5.62 (0.90) |
| | Placebo (9) | 6.64 (0.75) | 5.66 (0.81) | 5.02 (0.81) |
| Dizziness | Galanthamine (11) | 9.05 (1.26) | 9.00 (1.79) | 8.79 (1.81) |
| | Placebo (9) | 6.47 (1.61) | 6.94 (1.78) | 7.52 (2.01) |

The changes on the visual analogue scales of all galanthamine treated patients during treatment has been assessed, both those patients randomly allocated to galanthamine and those transferred from placebo, during the total eight weeks of the trial. These data are presented in Table 6.2.

TABLE 6.2

MEANS (STANDARD ERRORS) OF GALANTHAMINE TREATED PATIENTS ON VISUAL ANALOGUE SCALES

| Scale | Baseline N = 19 | 1 Week N = 19 | 2 Weeks N = 19 | 4 Weeks N = 18 | 8 Weeks N = 17 |
|---|---|---|---|---|---|
| Sleep | 19.45 (1.83) | 17.26 (1.68) | 15.51 (1.01) | 11.89 (1.95) | 10.88 (1.93) |
| Fatigue | 28.00 (1.28) | 26.63 (1.77) | 20.64 (2.09) | 17.42 (2.15) | 17.81 (2.21) |
| Myalgia | 16.32 (0.69) | 14.25 (0.89) | 11.24 (1.12) | 12.01 (1.15) | 10.51 (0.98) |
| Work | 9.21 (0.83) | 10.22 (1.07) | 8.21 (1.17) | 7.40 (1.25) | 7.34 (1.12) |
| Memory | 5.10 (0.64) | 5.41 (0.61) | 4.79 (0.59) | 4.33 (0.70) | 4.50 (0.68) |
| Dizziness | 8.39 (1.18) | 8.96 (1.40) | 6.94 (1.40) | 6.30 (1.32) | 4.77 (1.23) |

Statistically significant changes during treatment are observed on the scales assessing sleep disturbance (p <0.001), fatigue (0.001), myalgia (p <0.001), work capacity/satisfaction (p <0.001), and dizziness (p <0.001).

Comparable data to those above on the average time per response on a visual search task are as follows in Table 6.3:

TABLE 6.3

| Baseline N = 19 | 1 Week N = 19 | 2 Weeks N = 18 | 4 Weeks N = 18 | 8 Weeks N = 17 |
|---|---|---|---|---|
| 6.79 (0.36) | 6.24 (0.40) | 5.51 (0.43) | 5.83 (0.40) | 5.25 (0.31) |

Statistical analysis demonstrates that changes during treatment on this variable are significant (F=4.356; 4/60, p <0.001).

Data from the Cognitive Failures Questionnaire are available for all galanthamine treated patients at baseline and after 6 and 8 weeks of treatment. These are presented in Table 6.4:

TABLE 6.4

| Baseline N = 19 | 4 Weeks N = 17 | 8 Weeks N = 17 |
| --- | --- | --- |
| 47.74 (3.56) | 40.94 (3.87) | 38.47 (3.71) |

Statistical analysis demonstrates that changes during treatment on this variable are significant (F=5.339; 2/30, p <0.001).

CONCLUSIONS

The present data appear to provide clear and consistent evidence in favour of the therapeutic efficacy of galanthamine in the treatment of CFS. This evidence is derived from an interpretation of the patients' overall self-evaluation of the beneficial effects of treatment, and form the fact that an experienced, "blind" clinician transferred all placebo patients to active treatment after only two weeks of treatment, and made a comparable switch to placebo treatment in only one patient receiving galanthamine. Additional evidence of the beneficial effects of galanthamine comes form the observed significant improvements on a visual search task (a well validated test of concentration and attention), and similar improvements on a questionnaire designed to evaluate cognitive failures.

EXAMPLE 6

Auditory Brain Stem Response

Methods

Electrical potentials caused by click-stimulation in the ears are measured with electrodes positioned outside on the head of the examined parson. In the configuration of the potentials are components from the brain stem and the brain.

Persons

A patient suffering from bipolar manio-depression in the depressive stats and a healthy person, respectively.

Drug

Tablet containing 10 mg galanthamine

DESCRIPTION OF DRAWINGS

FIGS. 1A, and 2A show that in the depressed patient, the auditory brain stem response without treatment has a much smaller, almost half, amplitude of the potential compared to the amplitude of the untreated healthy person.

Furthermore, FIGS. 1A and 1B show a dramatically increase of the amplitude in the treated depressive patient compared to untreated persons.

Figure 2A:
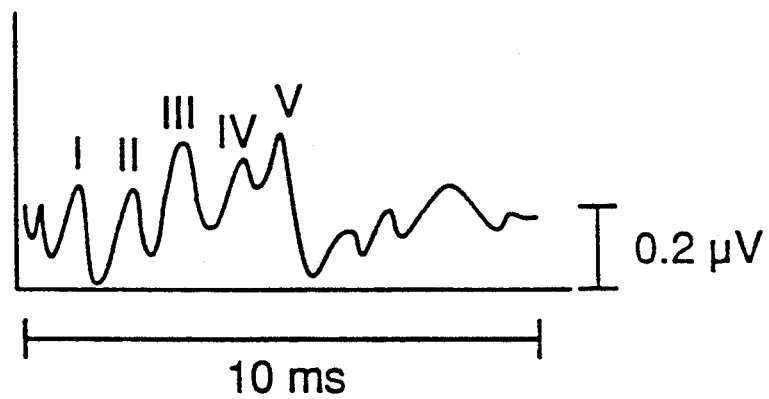
Figure 2B:
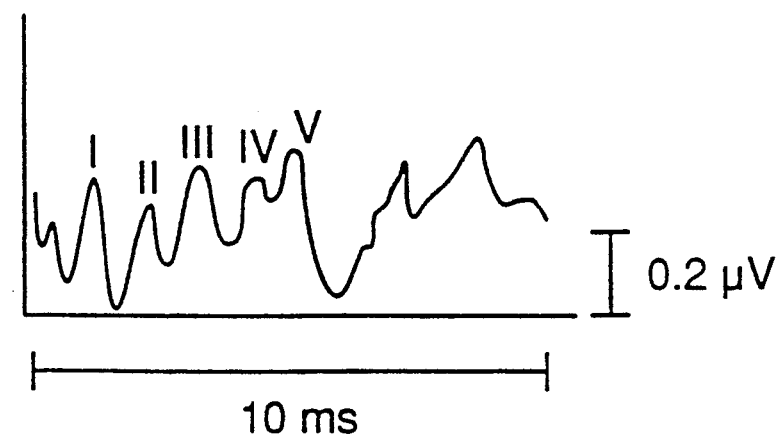

Also, from FIGS. 2A and 2B it is seen that the potentials do not change from the untreated person to the treated person.

Conclusion

From the results in the depressed person it is seen that the potentials change after treatment with galanthamine, such as explained above. This means that galanthamine must be able to cross the blood-brain barrier, since it is possible to inhibit in synapsis in the brain stem, which is positioned on the "brain side" of the blood-brain barrier.

LEGENDS TO FIGURES

Figure 1A:
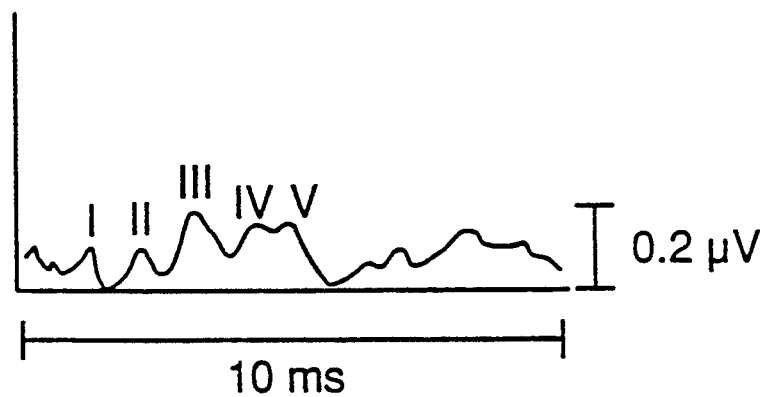
FIGS. 1A, 1B, 2A and 2B show the potentials from a depressive patient and a healthy person, both treated and untreated.

FIG. 1A shows the auditory evoked response of a depressed patient (a manio depressed patient in the depressed state) without treatment with galanthamine.

Figure 1B:
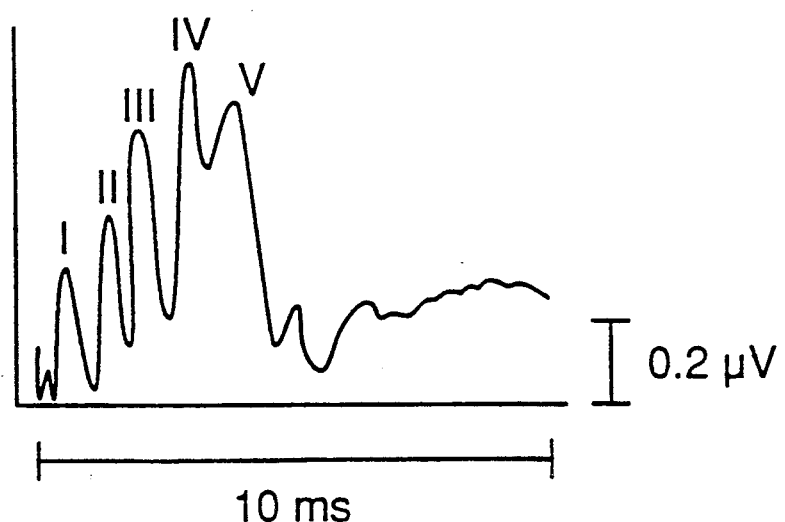

FIG. 1B shows the auditory evoked response of a depressed patient (the same as in FIG. 1A) 2 hours after treatment with 10 mg of galanthamine.

FIG. 2A shows the auditory evoked response of a healthy person without treatment with galanthamine.

FIG. 2B shows the auditory evoked response of a healthy person (the same as in FIG. 2A) 2 hours after treatment with 10 mg of galanthamine.

I claim:

1. A method for the treatment of a fatigue syndrome, comprising administering, to a patient in need thereof, an effective amount of a pharmaceutically acceptable cholinesterase inhibitor or a prodrug therefor.

2. A method according to claim 1 wherein the fatigue syndrome is a severe fatigue syndrome.

3. A method according to claim 1, wherein the fatigue syndrome is the Chronic Fatigue Syndrome.

4. A method according to claim 3, wherein the Chronic Fatigue Syndrome, in addition to the fatigue symptom, comprises one or more symptoms selected from sleep disturbances, myalgia, mood disturbances, lack of concentration and dizziness.

5. A method according to claim 1, wherein the fatigue syndrome is a Post-infectious Fatigue Syndrome.

6. A method according to claim 1, wherein the fatigue syndrome is the fatigue syndrome associated with human immunodeficiency virus (HIV) infection.

7. A method according to claim 1, wherein the fatigue syndrome is the fatigue syndrome associated with preclampsis.

8. A method according to claim 1, wherein the cholinesterase inhibitor is selected from the group consisting of galanthamine and galanthamine derivatives, norgalanthamine and norgalanthamine derivatives, epigalanthamine and epigalanthamine derivatives, physostigmine, tacrine and tacrine analogues, fasciculin, metrifonate, heptyl-physostigmine, norpyridostigmine, norneostigmine, and huperzine, or a prodrug therefor.

9. A method according to claim 1, in which the cholinesterase inhibitor is an acetylcholinesterase inhibitor which is active substantially selectively at nicotinic receptor sites.

10. A method according to claim 1, in which the acetylcholinesterase inhibitor is one which has an at least 10-fold selectivity for acetylcholinesterase as opposed to butyrylcholinesterase.

11. A method according to claim 10, in which the acetylcholinesterase inhibitor is one which has an at least 20-fold selectivity for acetylcholinesterase as opposed to butyrylcholinesterase.

12. A method according to claim 10, in which the acetylcholinesterase inhibitor is one which has an at least 40-fold selectivity for acetylcholinesterase as opposed to butyrylcholinesterase.

13. A method according to claim 9, in which the acetylcholinesterase inhibitor is one which, upon administration in an amount of 10 mg to a healthy adult, results in inhibition of at least 40% of the acetylcholinesterase activity in erythrocytes from the adult and no substantial inhibition of butyrylcholinesterase therein.

14. A method according to claim 13, in which the acetylcholinesterase inhibitor is one which, when administered in an amount of 10 mg to an adult, results in inhibition of at least 50% of the acetylcholinesterase activity in erythrocytes from the adult.

15. A method according to claim 1, in which the cholinesterase inhibitor is one which is capable of passing the blood-brain barrier in humans.

16. A method according to claim 1, in which the cholinesterase inhibitor is one which, upon administration to a human, increases the cortisol level in the human.

17. A method according to claim 1, in which the cholinesterase inhibitor is galanthamine or a salt, derivative or functional equivalent thereof.

18. A method according to claim 17, in which the functional equivalent is a compound which is an acetylcholinesterase capable of passing the blood brain barrier, which has an at least 10-fold selectivity for acetylcholinesterase as opposed to butyrylcholinesterase.

19. A method for the treatment of a fatigue syndrome, comprising administering, to a patient in need thereof, an effective amount of a galanthamine or a galanthamine salt or a galanthamine derivative.

20. A method according to claim 19, in which the compound is a galanthamine derivative of the general formula II

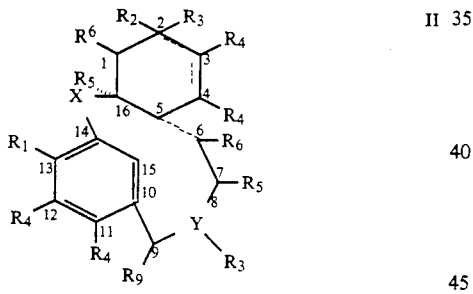

wherein the broken line represents an optionally present double bond in one or the two of the positions shown,
$R_1$ and $R_2$ are each selected independently from the group consisting of hydrogen, hydroxyl, amino or alkylamino, cyano, sulfhydryl, alkoxy of 1–6 carbon atoms, alkylthio, aryloxy, arylthio, $R_5$-substituted aryloxy, $R_5$-substituted arylthio, aralkoxy, an aliphatic or aryl carbamyl group wherein the aliphatic or aryl moiety may be $R_5$ substituted or unsubstituted, aralkylthio, $R_5$-substituted aralkoxy, $R_5$-substituted aralkylthio, aryloxymethyl, $R_5$-substituted aryloxymethyl, alkanoyloxy, hydroxy-substituted alkanoyloxy, benzoyloxy, $R_5$-substituted benzoyloxy, aryloxycarbonyl and $R_5$-substituted aryloxycarbonyl, $R_1$ may also be alkyl of up to 14 carbon atoms, or hydroxymethyl, $R_2$ may also be carboxymethyl, provided that at least one of $R_1$ and $R_2$ is hydroxy, amino or alkylamino unless $R_8$ is hydroxymethyl,
$R_3$ is hydrogen, straight or branched chain alkyl of 1–6 carbon atoms, cycloalkylmethyl, phenyl, $R_5$-substituted phenyl, alkylphenyl, $R_5$-substituted alkylphenyl, heterocyclyl selected from α- or β-furyl, α- or β-thienyl or thenyl, pyridyl, pyrazinyl, and pyrimidyl, alkyl-heterocyclyl or R'-substituted heterocyclyl, where R' is alkyl or alkoxy,
each $R_4$ is independently selected from hydrogen, hydroxyl, sulfhydryl, alkyl, aryl, aralkyl, alkoxy, mercaptoalkyl, aryloxy, thiaryloxy, alkaryloxy, mercaptoalkaryl, nitro, amino, N-alkylamino, N-arylamino, N-alkarylamino, fluoro, chloro, bromo, iodo, and trifluoromethyl,
$R_5$ is selected from the same groups as $R_4$,
$R_6$ is hydrogen, halo, trifluoromethyl or alkyl of 1 to 4 carbon atoms with the proviso that when $R_6$ is in position 7 or 9, it is not halo,
$R_8$ is hydrogen or hydroxymethyl,
$R_9$ is hydrogen or alkyl of 1 to 6 carbon atoms, or when $R_2$ is hydroxyl, $R_9$ may be a moiety of formula I wherein $R_9$ is hydrogen and $R_2$ is a linking bond; or
$R_2$ and $R_9$ may jointly form semicarbazone,
X is oxygen or $NR_5$,
Y is nitrogen or phosphorus,
and methylendioxy derivatives thereof with the proviso that when X is O, $R_3$ is not methyl when $R_1$ is methoxy, $R_2$ is hydroxy, and all $R_4$ are hydrogen,
or a pharmaceutically acceptable acid addition salts thereof.

21. A method according to claim 19, in which the compound is galanthamine or a derivative of galanthamine and has the formula I

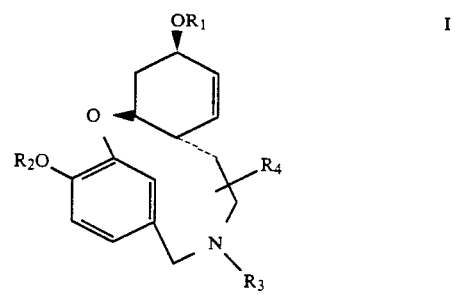

wherein
$R^1$ and $R^2$ which may be the same or different each represents a hydrogen atom or an acyl group, such as a lower alkanoyl group, e.g. an acetyl group or a straight-chained or branched alkyl group, e.g. methyl, ethyl, propyl, or isopropyl;
$R^3$ is a straight or branched chain alkyl, alkenyl or alkaryl group which is optionally substituted by a halogen atom or a cycloalkyl, hydroxy, alkoxy, nitro, amino, aminoalkyl, acylamino, heteroaryl, heteroaryl-alkyl, aroyl, aryolalkyl or cyano group; and
$R^4$ represents a hydrogen or halogen atom attached to at least one of the ring carbons of the tetracyclic skeleton, with the proviso that when $R_4$ is in a position neighbouring the nitrogen atom, then $R_4$ is different from halogen, and salts thereof, such as a hydrobromide, hydrochloride, methylsulphate or methiodide.

22. A method according to claim 19, wherein the galanthamine salt is galanthamine hydrobromide.

23. A method according to claim 19, wherein the fatigue syndrome is a severe fatigue syndrome.

24. A method according to claim 23, wherein the fatigue syndrome is the Chronic Fatigue Syndrome.

25. A method according to claim 24, wherein the Chronic Fatigue Syndrome, in addition to the fatigue symptom, comprises one or more symptoms selected from sleep disturbances, myalgia, mood disturbances, lack of concentration and dizziness.

26. A method according to claim 23, wherein the fatigue syndrome is a Post-infectious Fatigue Syndrome.

27. A method according to claim 23, wherein the fatigue syndrome is the fatigue syndrome associated with human immunodeficiency virus (HIV) infection.

28. A method according to claim 23, wherein the fatigue syndrome is the fatigue syndrome associated with preeclampsia.

29. A method according to claim 19, wherein the galanthamine derivative is one which is able to cross the blood brain barrier in humans.

30. A method according to claim 19, wherein the cholinesterase inhibitor or the galanthamine or the galanthamine salt or the galanthamine derivative is administered in the form of a pharmaceutical composition which is a tablet, a capsule, a sustained release capsule comprising micro capsules of the active ingredient, a solution or suspension, a plaster for transdermal application, or a suppository.

31. A method according to claim 19, in which the cholinesterase inhibitor or the galanthamine or the galanthamine salt or the galanthamine derivative is administered parenterally at a dosage which is equipotent with 0.1–1,000 mg of galanthamine hydrobromide per day, such as 5–1,000 mg of galanthamine hydrobromide.

32. A method according to claim 31, in which the cholinesterase inhibitor is administered in a dosage which is equipotent with to 10–500 mg galanthamine hydrobromide per day, such as 50–300 mg per day.

33. A method according to claim 32, in which the cholinesterase inhibitor is administered in a dosage which is equipotent with 10–50, in particular 10–30, mg galanthamine hydrobromide per day.

34. A method according to claim 1, in which the cholinesterase inhibitor is administered orally in a dosage which is equipotent with 5–2000 mg galanthamine hydrobromide per day.

35. A method according to claim 33, in which the cholinesterase inhibitor is administered at a dosage which is equipotent with 10–500 mg galanthamine hydrobromide per day.

36. A method according to claim 34, in which the cholinesterase inhibitor is administered at a dosage which is equipotent with 10–50 mg, such as 10–30 mg, of galanthamine hydrobromide per day.

* * * * *

UNITED STATES PATENT AND TRADEMARK OFFICE
CERTIFICATE OF CORRECTION

PATENT NO. : 5,312,817
DATED : May 17, 1994
INVENTOR(S) : SNORRASON

Page 1 of 3

It is certified that error appears in the above-identified patent and that said Letters Patent is hereby corrected as shown below:

Column 11, lines 10-20, delete the chemical structure and replace it with:

--

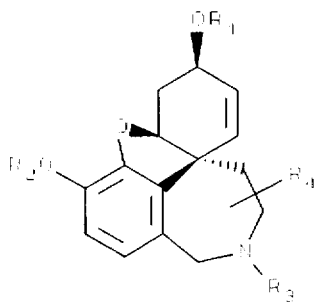

--;

lines 55-65, delete the chemical structure and replace it with:

--

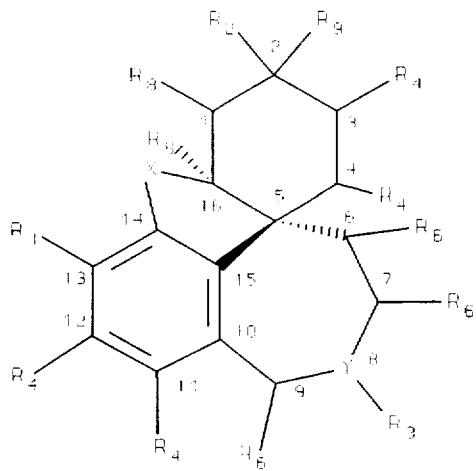

--;

UNITED STATES PATENT AND TRADEMARK OFFICE
CERTIFICATE OF CORRECTION

PATENT NO. : 5,312,817
DATED : May 17, 1994
INVENTOR(S) : SNORRASON

It is certified that error appears in the above-identified patent and that said Letters Patent is hereby corrected as shown below:

line 66, after "line" insert --between carbons 3 and 4--;
line 67 (last line), delete "in one or the two of the positions shown".

Column 12, lines 36-37, delete "R7 is selected from the same groups as $R_4$ or may be hydroxyalkyl of 1-2 carbon atoms,";
lines 40-41, delete "formula I" and insert --formula II--.

Claim 20, column 21, lines 35-45, delete the chemical structure and replace it with:
--

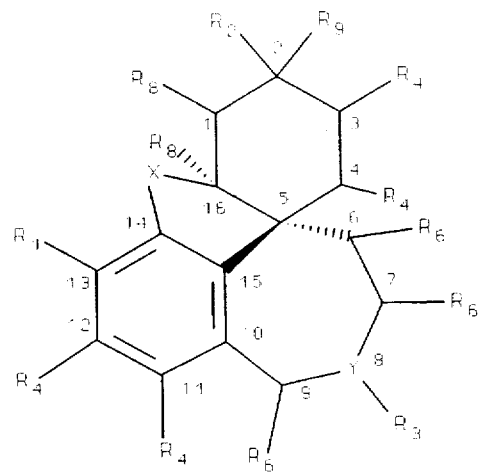

--;

column 21, line 47 (the first line of text after the chemical structure), after "line" insert --between carbon atoms 3 and 4--;

UNITED STATES PATENT AND TRADEMARK OFFICE
CERTIFICATE OF CORRECTION

PATENT NO. : 5,312,817
DATED : May 17, 1994
INVENTOR(S) : SNORRASON

It is certified that error appears in the above-indentified patent and that said Letters Patent is hereby corrected as shown below:

column 21, line 48, delete "in one or the two of the positions shown";

column 22, lines 17-18 (in the definition of $R_9$), delete "formula I" and insert --formula II--.

Claim 21,    column 22, lines 35-45, delete the chemical structure and replace it with:

-- 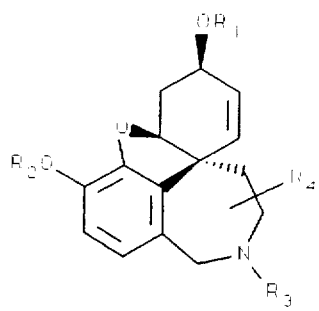 --.

Signed and Sealed this

Twenty-first Day of July, 1998

*Attest:*

BRUCE LEHMAN

*Attesting Officer*      Commissioner of Patents and Trademarks